United States Patent [19]
Eckels et al.

[11] Patent Number: 4,729,765
[45] Date of Patent: Mar. 8, 1988

[54] METHOD OF USING MECONIUM ASPIRATOR COMPONENTS

[76] Inventors: John F. Eckels, 2762 Goldfield, Simi Valley, Calif. 93063; Kenneth C. Cook, 27517 Arcoy Ave., Canyon Country, Calif. 91351

[21] Appl. No.: 944,190

[22] Filed: Dec. 22, 1986

[51] Int. Cl.$^4$ ............................................. A61M 31/00
[52] U.S. Cl. .................. 604/54; 128/207.16; 604/119
[58] Field of Search ............... 604/118, 119, 902, 54; 285/177, 332; 128/207.14, 207.16

[56] References Cited

U.S. PATENT DOCUMENTS

| | | | |
|---|---|---|---|
| 2,185,725 | 1/1940 | Elliot | 285/177 |
| 3,319,628 | 5/1967 | Halligan | 604/119 |
| 3,610,242 | 10/1971 | Sheridan et al. | 604/119 |
| 4,275,724 | 6/1981 | Behrstock | 128/207.14 |
| 4,351,328 | 9/1982 | Bodai | 128/202.16 |

OTHER PUBLICATIONS

Davol-Bard Catalog Cit.

Primary Examiner—C. Fred Rosenbaum
Assistant Examiner—J. L. Kruter
Attorney, Agent, or Firm—William W. Haefliger

[57] ABSTRACT

A multi-component meconium aspirator, adapter and endotracheal tube are manipulated, by one-handed use, to keep them assembled and to control suction level, during meconium removal from an infant.

4 Claims, 2 Drawing Figures

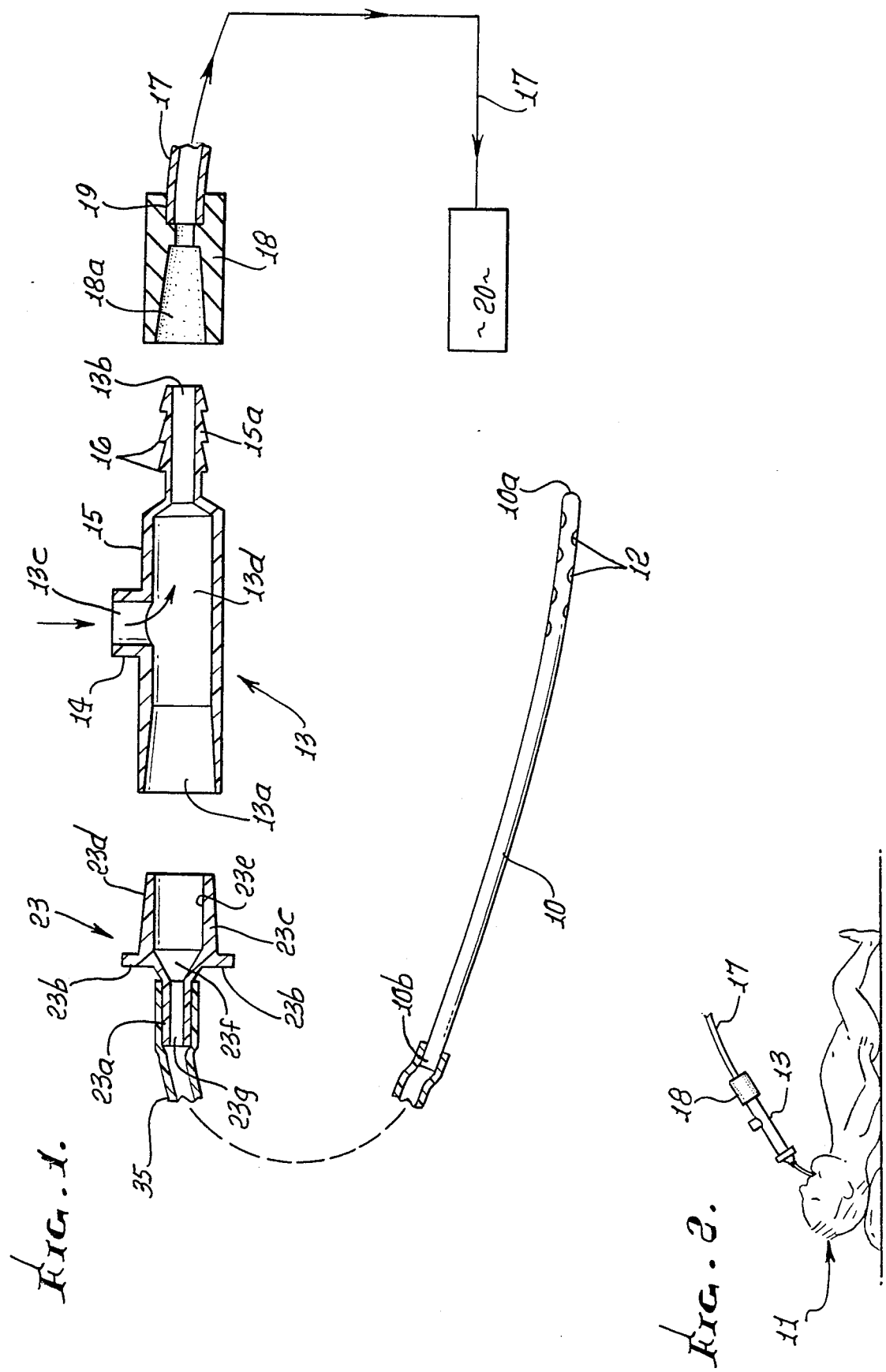

METHOD OF USING MECONIUM ASPIRATOR COMPONENTS

BACKGROUND OF THE INVENTION

This invention relates generally to meconium removal from infants and more particularly concerns improved method and apparatus for such removal.

The problem of meconium removal from infant's lungs and air ways occurs for example when infants are stressed during birth. If not thoroughly removed, the remanent meconium can lead to infection, lung damage, and breathing difficulty. There is need for method and apparatus to insure such removal.

SUMMARY OF THE INVENTION

It is a major object of the invention to provide method and apparatus meeting the above need. Basically, the method of the invention involves employment of an aspirator together with an endo-tracheal tube, the aspirator having an inlet end, an outlet end, and a side inlet; and the method includes the steps:

(a) inserting one end of the endo-tracheal tube into the infant's air-way,
(b) opposite end of the tube being connected to the aspirator inlet outside the infant's air way,
(c) applying suction to the aspirator outlet to draw air into the aspirator through the side inlet, and
(d) controllably closing said inlet to increase suction application to said one end of the endo-tracheal tube thereby to controllably draw meconium fluid in said airway into the tube inlet for withdrawal through the aspirator inlet and outlet, while at the same withdrawing said tube from the infant's air-way.

As will appear, an adapter is typically provided for connecton between the tube and aspirator after the tube is inserted into the airway, so that two functions can then be carried out by grasping the aspirator; these functions being withdrawal of the tube from the airway by pulling on the aspirator, and at the same time thumb control of the aspirator side inlet to controllably apply suction to the airway via the ET tube, so that too much suction is avoided, and just the right amount of suction is applied under control of the physician, as the tube is withdrawn, to remove the meconium.

In its apparatus aspect, the invention includes:

(a) an endo-tracheal tube one end of which is insertible into the infant's airway, the tube having an opposite end outside the airway,
(b) an aspirator having an end inlet and outlet, and a side inlet, the aspirator end outlet being connected to a suction tube via which suction is applicable to the aspirator to draw air into the aspirator via said side inlet, and
(c) the aspirator end inlet then connected to the opposite end of the endo-tracheal tube for withdrawing the tube from the airway while the aspirator side inlet is variably controlled to variably apply suction to said airway to remove meconium therefrom via the tube and aspirator.

An adapter is typically connected between the ET tube and the inlet end of the aspirator; and the aspirator and adapter have telescoping annular tapers which are frictionally interfitted to establish the connection of the adapter to the aspirator. Also, a suction tube is typically connected to the outlet end of the aspirator, and to which a source of suction is connected.

These and other objects and advantages of the invention, as well as the details of an illustrative embodiment, will be more fully understood from the following specification and drawings, in which:

DRAWING DESCRIPTION

FIG. 1 is an exploded side elevation showing apparatus incorporating the invention; and FIG. 2 is an elevation showing method of using an aspirator and endo-tracheal tube, in accordance with the invention.

DETAILED DESCRIPTION

In FIG. 1, apparatus for effecting meconium removal from an infant's lungs includes an endo-tracheal tube 10 one end 10a of which is insertible into an airway (such as the throat and lung entrance) of an infant 11. See FIG. 2. The ET tube end 10a may contain ports 12 for entrance of fluid. The tube has an opposite end 10b outside the air-way, and to which an aspirator 13 is connected. The latter is tubular, and has an inlet end 13a, and outlet end 13b, and a side inlet 13c to main passage 13d in the aspirator. Inlet 13c is formed by a stub tubing 14 integral with the aspirator body 15, which may consist of molded plastic material.

The outlet end 13b of the aspirator is shown as defined by reduced diameter body portion 15a, defining barbs 16. Plastic suction tubing 17 is connected to body portion 15a, as by means of a rubber or vinyl fitting 18 that has a tapered mouth 18a fitted over the barbs 16 to retain the fitting in place. Tubing 17 is attached at 19 to the fitting. A source of regulated suction is shown at 20, the amount of suction being between 60 and 90 mm. of mercury, and preferably about 80 mm. of mercury. When so connected, air is drawn into the aspirator passage 13d, via side inlet 13c, and flows to tubing 17.

A connection between the ET tube 10 and the aspirator 13 is defined by an adapter 23, typically connected between the ET tube end 10b and the inlet end 13a of the aspirator 13. The connection is such that the aspirator serves two functions, namely, it is gripped manually to pull the ET tube from inserted position in the airway, and at the same time the user's thumb extends over inlet port 13c i.e. over rim 13e, and controls the amount of air flowing to suction tube 17, thereby to control aspiration of the meconium fluid from the airway, via ET tube 10 and the aspirator inlet 13a. In this way, the full force of suction to the infant's lungs is avoided, and may be carefully controlled by the physician.

Adapter 23 is tubular, and has a reduced tubular end portion 23a to which end 10b of the ET tube is connected as by tubing 35 (or tube 10 may be directly connected to end portion 23a) and two diametrically opposed flanges 23b. Also, the adapter has an enlarged annular portion 23c projecting toward the aspirator to interfit telescopically the end of the aspirator that defines opening 13a. Portion 23c has an outer annular surface 23d that tapers rightwardly toward the aspirator to rearwardly and frictionally interfit the correspondingly opposed shallow tapered bore 13g of the aspirator, establishing a quick connection enabling pull-out of the ET tube from the infant's airway by pulling on the aspirator. Finger pressure on the two flanges 23b assures rapid direct interfit of surfaces 23d and 13g, as well as slip-on frictional connection between tube end 10b and adapter portion 23a. Also the adapter and aspirator are later pulled apart by applying finger pressure to the flanges.

The diameter cylindrical bore 23e of the adapter is close to that of the aspirator passage 13d; and a tapered diffuser section 23f of the adapter connects reduced diameter passage 23g with bore 23e, for smooth flow. The adapter may also be made of vinyl plastic material. The outer diameter of tapered portion 23c is about 13 mm. for example.

The method of use includes the steps (a) inserting one end of the endo-tracheal tube into the infant's airway, (b) the opposite end of the tube being connected to the aspirator inlet outside the infant's airway, (c) applying suction to the aspirator outlet to draw air into the aspirator through the side inlet, and (d) controllably closing said inlet to increase suction application to said one end of the endo tracheal tube thereby to controllably draw meconium fluid in said airway into the tube inlet for withdrawal through the aspirator inlet and outlet, while also withdrawing said tube from the infant's airway.

Also, the adapter is typically connected to the aspirator after the tube is inserted into the infant's airway, and while suction is applied to the aspirator; and the suction tube is connected to the aspirator prior to connection of the adapter to the aspirator.

We claim:

1. The method of using an aspirator, an adapter and an endo-tracheal tube on an infant for meconium removal, the aspirator having an end inlet and outlet and a side inlet, that includes:

(a) providing an aspirator, an adapter and an endo-tracheal tube, (b) inserting one end of the endo-tracheal tube into the infant's air-way, the opposite end of the tube being connected to the aspirator inlet outside the infant's air way, (c) applying suction to the aspirator outlet to draw air into the aspirator through the side inlet, and (d) connecting said adapter between the tube and the aspirator after the tube is inserted into the infant's airway, and while suction is applied to the aspirator, the adapter and aspirator having telescoping annular tapers, and said connection including endwise interfitting said tapers, frictionally, to establish said connection of the adapter to the aspirator, (e) said adapter having oppositely outwardly projecting external flange means, and including urging said flange means toward the aspirator to establish said frictional interfit rapidly and to maintain the interfit during use of the aspirator, while simultaneously adjusting the suction level through said aspirator side inlet by the user's one-handed controlled manipulation of the flange means and side inlet, (f) and controllably closing said side inlet to increase suction application to said one end of the endo tracheal tube, thereby to controllably draw meconium fluid in said airway into the tube inlet for withdrawal through the aspirator end inlet and outlet, while also withdrawing said tube from the infant's airway.

2. The method of claim 1 that includes providing a suction tube to which suction is applied, and connecting the suction tube to the aspirator prior to connection of the adapter to the aspirator.

3. The method of claim 1 wherein said removal of the endo-tracheal tube from the infant is carried out by manually gripping the aspirator and pulling it endwise, while controllably covering the aspirator side inlet with the thumb.

4. The method of claim 1 wherein an elastomeric coupling is provided between the aspirator and suction tube, said connection of the suction tube to the aspirator carried out by endwise telescopicaly interfitting the coupling and an end portion of the aspirator which defines barbs, to capture the coupling.

* * * * *